United States Patent [19]

Hill

[11] Patent Number: 4,716,230
[45] Date of Patent: Dec. 29, 1987

[54] CERTAIN BIS(DI-2 OR 4-PYRIDYL-PHOSPHINO) ALKANES #10 HAVING ANTI-TUMOR PROPERTIES

[75] Inventor: David T. Hill, North Wales, Pa.

[73] Assignee: Smithkline Beckman Corporation, Philadelphia, Pa.

[21] Appl. No.: 843,886

[22] Filed: Mar. 25, 1986

Related U.S. Application Data

[63] Continuation-in-part of Ser. No. 723,778, Apr. 16, 1985, abandoned.

[51] Int. Cl.$^4$ .......................... C07F 9/58; A61K 33/42
[52] U.S. Cl. .......................................... 546/21; 549/6; 514/89; 514/95; 514/99
[58] Field of Search ............................. 546/21; 514/89

[56] References Cited

FOREIGN PATENT DOCUMENTS

0151046A3  8/1985  European Pat. Off. ............ 514/102
0164970A2 12/1985  European Pat. Off. ............ 514/102

OTHER PUBLICATIONS

Remers, Antineoplastic Agents, pp. 68-76, Wily-Interscience Publishers, (1984).
Shaw et al., *Inorganica Chimica Acta*, 123, 213-216, (1986).
Eggleston et al., *Inorganica Chimica Acta*, 108, 221-226 (1985).
Mirabelli et al., *Biochemical Pharmacology*, 35(9), 1435-1443 (1986).
Mirabelli et al., *Biochemical Pharmacology*, 35(9), 1427-1433 (1986).
Mirabelli et al., *J. Med. Chem.*, 29(2), 218-223 (1986).
Hill et al., Abstract #204, American Chemical Society.
Berners-Price et al., Abstract #244, American Chemical Society.
Johnson et al., Abstract #1001, *Proceedings of AACR*, 26, Mar. 1985.
Snyder et al., Abstract #1007, *Proceedings of AARC*, 25, Mar. 1985.
Mirabelli et al., Abstract #1008, *Proceedings of AARC*, 26, Mar. 1985.
Mirabelli et al., Abstract #1114, *Proceedings of AACR*, 27, Mar. 1986.
Johnson et al., Abstract #1115, *Proceedings of AACR*, 27, Mar. 1986.
Hill et al., Abstract #14, 190th American Chemical Society.
Struck et al., J. Med. Chem., 9, 414-417 (1966).
Mirabelli et al., Proceedings of AACR, Mar. 1984, No. 1455, p. 367 (1984).
Mirabelli et al., Cancer Research, 45, 32-39 (1985).

*Primary Examiner*—Alan L. Rotman
*Attorney, Agent, or Firm*—Carol G. Canter; Edward T. Lentz; Alan D. Lourie

[57] ABSTRACT

Heterocyclic phosphine compounds, pharmaceutical compositions containing an effective, tumor cell growth-inhibiting amount of such a compound, and a method for treating tumor cells sensitive to such a compound which comprises administering a tumor cell growth-inhibiting amount of such a compound to an animal afflicted by said tumor cells.

4 Claims, No Drawings

CERTAIN BIS(DI-2 OR 4-PYRIDYL-PHOSPHINO) ALKANES #10 HAVING ANTI-TUMOR PROPERTIES

CROSS-REFERENCE TO RELATED APPLICATION

This is a continuation-in-part of application Ser. No. 723,778, filed Apr. 16, 1985, abandoned.

BACKGROUND OF THE INVENTION

This invention relates to novel heterocyclic phosphine compounds which have tumor cell growth-inhibiting activity, pharmaceutical compositions containing an effective, tumor cell growth-inhibiting amount of such a novel compound, and a method for treating tumor cells sensitive to such a compound by administering tumor cell growth-inhibiting amounts of such a novel compound to a host animal afflicted by such tumor cells.

The compounds of this invention are not known. Struck et al., J. Med. Chem., 9, 414–416 (1966) disclose cytotoxic activity for 1,2-bis(diphenylphosphino)ethane. The Struck et al. reference does not disclose or suggest the compounds of this invention or that they have tumor cell growth-inhibiting activity.

SUMMARY OF THE INVENTION

This invention relates to heterocyclic phosphine compounds of the formula:

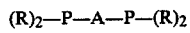
$(R)_2$—P—A—P—$(R)_2$  FORMULA (I)

wherein:

R is the same and is 2-pyridyl, 4-pyridyl, 2-thienyl or 2-furyl; and

A is a straight or branched alkanediyl chain of from one to six carbon atoms.

This invention also relates to a pharmaceutical composition which comprises an effective, tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of Formula (I).

Another aspect of this invention relates to a method of inhibiting the growth of animal tumor cells sensitive to a compound of Formula (I) which comprises administering to an animal afflicted with said tumor cells, an effective, tumor cell growth-inhibiting amount of a compound of Formula (I).

DETAILED DESCRIPTION OF THE INVENTION

All the compounds of Formula (I) can be prepared by methods available to one skilled in the art.

Generally, the compounds of Formula (I) can be prepared by reacting the appropriate heterocycle in an anhydrous ethyl ether with an organolithium reagent, such as n-butyl lithium in a non reactive organic solvent, with the appropriate compound of the formula:

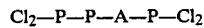
$Cl_2$—P—A—P—$Cl_2$  FORMULA (II)

wherein A is as defined above.

All the necessary heterocycles, organo lithium reagents and Formula (II) compounds are available from commercial sources, for example from Strem Chemicals, Inc., Danvers, Mass.

As stated above, the compounds of Formula (I) have tumor cell growth-inhibiting activity which has been demonstrated in at least one animal tumor model.

P388 lymphocytic leukemia is currently the most widely used animal tumor model for screening for antitumor agents and for detailed evaluation of active compounds. This tumor system is widely accepted as an antitumor agent screening tool because it is sensitive to virtually all of the clinically active antineoplastic agents; quantitative and reproducible; amenable for large-scale screening; and predictive for activity in other animal tumor models. Drugs that are highly active in intraperitoneal (ip) P388 leukemia are generally active in other tumor models as well. The antitumor activity of the compounds of Formula (I) is demonstrated in the P388 leukemia mouse model employing the following protocol:

$10^6$ P388 leukemia cells are inoculated ip in B6D2F$_1$ mice. Twenty-four hours later, if the tumor inoculum proves to be free of bacterial contamination (as determined by 24 hours incubation in thioglycollate broth), animals are randomized into groups of 6 and housed in shoebox cages. The compound to be evaluated is dissolved in a minimal volume of either N,N-dimethylacetamide (DMA) or 95% ethanol (depending upon solubility). An equal volume of saline is added; if the drug comes out of solution an equal volume of polyethoxylated castor oil is added and then saline qs to a concentration such that the desired dose is delivered in 0.5 ml. The final concentration of DMA, ethanol and polyethoxylated castor oil is ≧10 percent. Dilutions for lower doses are made with saline so there is a decreasing proportion of organic solvents in the vehicle with decreasing dosage. These vehicles provide soluble formulations (or suspensions). Formulations are prepared immediately prior to injection. The compound is administered ip on Days 1 through 5 (i.e. treatment is initiated 24 hrs after tumor inoculation). Each experiment includes three groups of 6 animals as untreated controls and animals treated with a positive control, cisplatin, at two dose levels. Animals are weighed as a group on Days 1, 5 and 9 and average weight change (Δwt.) is used as a reflection of toxicity. Each experiment also includes an inoculum titration—groups of 8 mice inoculated ip with $10^5$ to $10^9$ P388 leukemia cells. The titration is used to calculate cell kill achieved by treatment with drugs. Animals are monitored daily for mortality and experiments are terminated after 45 days. The endpoint is median survival time (MST) and increase in lifespan (ILS) which is the percentage of increase in MST relative to untreated controls. Untreated controls inoculated ip with $10^6$ P388 leukemia cells generally survive for a median of 9 or 11 days. A drug is considered active if it produces ≧25 percent ILS.

A summary of the evaluation of several compounds of Formula (I) in the in vivo ip P388 model is shown in the following Table A.

TABLE A

| | $(R)_2$-P-A-P-$(R)_2$ FORMULA (I) | | | |
|---|---|---|---|---|
| Compound Number | R | A | MTD[a] (mg/kg) | ILS (max)[b] (%) |
| 1 | 2-pyridyl | $(CH_2)_2$ | 16 | 30/20 |
| 2 | 4-pyridyl | $(CH_2)_2$ | 32 | 35/37 |
| 3 | 2-thienyl | $(CH_2)_2$ | 16 | 60/55 |

TABLE A-continued (R)₂-P-A-P-(R)₂
FORMULA (I)

| Compound Number | R | A | MTD[a] (mg/kg) | ILS (max)[b] (%) |
|---|---|---|---|---|
| 4 | 2-furyl | (CH₂)₂ | 64 | 60/30/50 |

[a] maximally tolerated dose for B6D2F female mice on an ip qD × 5 regimen.
[b] maximum increase in lifespan produced in mice bearing ip P388 leukemia (figures separated by slashes indicate data generated in seperate experiments).

Based on the data set forth in Table A, compounds of Formula (I) showed significant antitumor activity in the in vivo ip P388 leukemia tumor assay.

The pharmaceutical compositions of this invention comprise an effective tumor cell growth-inhibiting amount of a compound of Formula (I) and an inert pharmaceutically acceptable carrier or diluent. These compositions are prepared in dosage unit form appropriate for parenteral administration.

Compositions according to the invention for parenteral administration include sterile aqueous or non-aqueous solutions, suspensions or emulsions. The composition may be in the form of a solution of the active ingredient in a minimal volume of dimethylacetamide or ethanol, for example 5% v/v, brought up to volume with peanut oil or normal saline solution. Polyethoxylated castor oil, for example 2 to 5% v/v, may also be used to solubilize the active ingredient. In addition, the composition may be in the form of a slurry with, for example, hydroxypropyl cellulose or other suitable suspending agent. As an emulsifying agent, lecithin for example may be used. The composition may also be provided in the form of a sterile solid which can be dissolved in a sterile injectable medium immediately before use.

Freireich et al., Cancer Chemo. Rept., 50, 219-244 (1966), compared the quantitative toxicity of 18 anticancer drugs in six species after correcting the data to a uniform schedule of treatment for five consecutive days. This analysis demonstrated that mouse, rat, dog, human, monkey and man have essentially the same maximum tolerated dose (MTD) when compared on a basis of mg/m² of body surface area. The study suggested that Phase I clinical trials could be safely initiated at a dose one-third the animal MTD. The mouse was as useful as any other species in this regard on which to base the calculation. The appropriate therapeutically effective dose for any compound of the invention can therefore be determined readily by those skilled in the art from simple experimentation with laboratory animals, preferably mice.

It will be appreciated that the actual preferred dosages of the compounds of Formula (I) used in the compositions of this invention will vary according to the particular compound being used, the particular composition formulated, the mode of administration and the particular site, host and disease being treated. The route of internal administration should be selected to ensure that an effective tumor cell growth-inhibiting amount of the compound of Formula (I) contacts the tumor. Optimal dosages for a given set of conditions can be ascertained by those skilled in the art using conventional dosage determination tests in view of the above experimental data. For parenteral adminstration the dose preferably employed is from about 15 to about 600 mg/m² of body surface per day for five days, repeated about every fourth week for four courses of treatment.

The method for inhibiting the growth of animal tumor cells sensitive to a compound of Formula (I) in accordance with this invention comprises administering to a host animal afflicted with said tumor cells, an effective tumor cell growth-inhibiting amount of a compound of Formula (I).

EXAMPLES

The following examples illustrate the chemical preparation of several compounds of Formula I which are used in the compositions and methods of this invention and as such are not to be construed as limiting the scope thereof. All temperatures are in degrees Centigrade.

EXAMPLE 1

1,2-Bis(di-2-pyridylphosphino)ethane

Under an argon atmosphere, 2-bromopyridine (30.9 g, 0.19 mole) in anhydrous ethyl ether (50 ml) was added to n-butyl lithium (0.19 mole) in hexane (73 ml) keeping the temperature below −50°. After stirring for 1 hour, an additional 7.5 g of 2-bromopyridine was added, and the mixture was stirred for 30 minutes. An ether solution (100 ml) of 1,2-bis(dichlorophosphino)ethane (10 g, 43 mmole), obtained from Strem Chemicals, Inc., Danvers, Mass., was added, and the mixture was stirred for 1 hour at −50°, and then allowed to warm to room temperature overnight. Saturated aqueous ammonium chloride was added and the mixture was stirred for 1 hour, the solid was collected and dissolved in chloroform, dried (Na₂SO₄), filtered and the solvent was removed to give a dark residue. The residue was treated with acetone, and then the acetone was cooled to give a light yellow solid (4.5 g). Recrystallization from acetone gave 2.64 g of the named product, melting point (m.p.) 134°-135°

EXAMPLE 2

1,2-Bis(di-4-pyridylphosphino)ethane

Under an argon atmosphere, 4-bromopyridine (30.9 g, 0.19 mole) in anhydrous ethyl ether (50 ml) was added to n-butyl lithium (0.19 mole) in hexane (73 ml) keeping the temperature below −50°. After stirring for 1 hour, an additional 7.5 g of 4-bromopyridine was added, and the mixture was stirred for 30 minutes. An ether solution (100 ml) of 1,2-bis(dichlorophosphino)ethane (10 g, 43 mmole), obtained from Strem Chemicals, Inc., Danvers, Mass., was added, and the mixture was warmed to room temperature overnight. After 18 hours at ambient temperature, aqueous saturated ammonium chloride was added and the solid was removed. The residual solid in the flask was collected, dissolved in chloroform, treated with activated carbon, filtered and the solvent removed. Flask chromatography (SiO₂, 7% methanol/methylene chloride) of the residue gave a small amount of the desired product, m.p. 183°-185°.

EXAMPLE 3

1,2-Bis(di-2-thienylphosphino)ethane)

Under argon at ambient temperature, thiophene (16 g, 0.19 mole) in anhydrous ethyl ether (50 ml) was added to a hexane (73 ml) solution of n-butyl lithium (0.19 moles) which had been diluted with ether (50 ml). After stirring for 1 hour, the mixture was cooled to 0°. Then 1,2-bis(dichlorophosphino)ethane (10 g, 0.043 mole), obtained from Strem Chemicals, Inc., Danvers, Mass., in ether (50 ml) was added, and the mixture was allowed to warm to room temperature and was stirred for 2 hours. Saturated aqueous ammonium chloride solution was added and the solid material collected. This was dissolved in chloroform, washed with water, dried (MgSO$_4$), filtered and the solvent concentrated to give a solid which was collected and dried to give 4.2 g, m.p. 108°–110°. Chromatography (SiO$_2$, 2:1 CCl$_4$/CH$_2$Cl$_2$) gave the named product in analytical purity after crystallization from ethanol; m.p. 114°–115°.

EXAMPLE 4

1,2-Bis(di-2-furylphosphino)ethane

Furan (12.9 g, 0.19 mole) in anhydrous ethyl ether (50 ml) was added to a hexane (73 ml) solution of n-butyl lithium (0.19 moles), diluted with ether (50 ml) and kept at ambient temperature. The mixture was stirred for 2 hours, cooled to 0°, and 1,2-bis-dichlorophosphino)ethane (10 g, 0.043 mole), obtained from Strem Chemicals, Inc., Danvers, Mass., in ether (50 ml) was added. The mixture was stirred for 18 hours and warmed to room temperature. Saturated aqueous ammonium chloride was added, and the mixture was stirred for 1 hour. The solid was removed. The mixture was extracted with ether, and then chloroform and the extracts were combined. The solid from the combined organic extract was removed and the solvent removed in vacuo. The residue was treated with hot hexane, cooled and the solid collected (4.7 g). Recrystallization from ethanol gave 1.5 g of the named product as needles, m.p. 94°–96°.

EXAMPLE 5

Using the procedure of Example 1 to react the appropriate heterocycle with the appropriate Formula (II) compound, the following compounds of Formula (I) are prepared:

a. 1,2-Bis(di-2-pyridylphosphino)methane
b. 1,2-Bis(di-2-pyridylphosphino)propane
c. 1,2-Bis(di-2-pyridylphosphino)butane
d. 1,2-Bis(di-2-pyridylphosphino)pentane
e. 1,2-Bis(di-2-pyridylphosphino)hexane
f. 1,2-Bis(di-4-pyridylphosphino)methane
g. 1,2-Bis(di-4-pyridylphosphino)propane
h. 1,2-Bis(di-4-pyridylphosphino)butane
i. 1,2-Bis(di-4-pyridylphosphino)pentane
j. 1,2-Bis(di-4-pyridylphosphino)hexane
k. 1,2-Bis(di-2-thienylphosphino)methane
l. 1,2-Bis(di-2-thienylphosphino)propane
m. 1,2-Bis(di-2-thienylphosphino)butane
n. 1,2-Bis(di-2-thienylphosphino)pentane
o. 1,2-Bis(di-2-thienylphosphino)hexane
p. 1,2-Bis(di-2-furylphosphino)methane
q. 1,2-Bis(di-2-furylphosphino)propane
r. 1,2-Bis(di-2-furylphosphino)butane
s. 1,2-Bis(di-2-furylphosphino)pentane
t. 1,2-Bis(di-2-furylphosphino)hexane

EXAMPLE 6

As a specific embodiment of a composition of this invention, an active ingredient, such as one part of the compound of Example 1, is dissolved in 5 parts of dimethylacetamide and 5 parts of polyethoxylated castor oil and then normal saline solution qs, and is administered parenterally in one dose of 30 mg/m$^2$ to a host animal afflicted with tumor cells sensitive to that compound.

What is claimed is:

1. A compound of the formula $$(R)_2-P-A-P-(R)_2$$

wherein:
R is the same and is 2-pyridyl or 4-pyridyl, and
A is a straight or branched alkanediyl chain of from one to six carbon atoms.

2. The compound of claim 1 wherein A is ethane-1,2-diyl.
3. The compound of claim 2 where R is 2-pyridyl.
4. The compound of claim 2 where R is 4-pyridyl.

* * * * *